US012642497B2

(12) United States Patent
Von Berg et al.

(10) Patent No.: US 12,642,497 B2
(45) Date of Patent: Jun. 2, 2026

(54) FLUOROSCOPIC POSITIONING GUIDANCE

(71) Applicant: KONINKLIJKE PHILIPS N.V., Eindhoven (NL)

(72) Inventors: Jens Von Berg, Hamburg (DE); Heiner Matthias Brueck, Poinneberg (DE); Sven Kroenke-Hille, Hamburg (DE); Daniel Bystrov, Hamburg (DE); Andre Goossen, Eldena (DE); Tim Philipp Harder, Ahrensburg (DE); Stewart Matthew Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 173 days.

(21) Appl. No.: 18/719,911

(22) PCT Filed: Dec. 17, 2022

(86) PCT No.: PCT/EP2022/086517
§ 371 (c)(1),
(2) Date: Jun. 14, 2024

(87) PCT Pub. No.: WO2023/117817
PCT Pub. Date: Jun. 29, 2023

(65) Prior Publication Data
US 2025/0040902 A1 Feb. 6, 2025

(30) Foreign Application Priority Data

Dec. 20, 2021 (EP) ..................................... 21216023

(51) Int. Cl.
*A61B 6/00* (2024.01)
*A61B 6/02* (2006.01)

(52) U.S. Cl.
CPC .............. *A61B 6/487* (2013.01); *A61B 6/027* (2013.01); *A61B 6/488* (2013.01); *A61B 6/5211* (2013.01); *A61B 6/545* (2013.01)

(58) Field of Classification Search
CPC ......... A61B 6/487; A61B 6/027; A61B 6/488; A61B 6/5211; A61B 6/545; A61B 6/0492; A61B 6/461; A61B 6/505; A61B 6/4441
See application file for complete search history.

(56) References Cited

U.S. PATENT DOCUMENTS

| | | | |
|---|---|---|---|
| 2016/0104312 A1 | 4/2016 | Zino | |
| 2022/0110593 A1* | 4/2022 | Kinoshita | .............. A61B 6/547 |

OTHER PUBLICATIONS

PCT International Search Report, International application No. PCT/EP2022/086517, Mar. 24, 2023.

(Continued)

*Primary Examiner* — Courtney D Thomas
(74) *Attorney, Agent, or Firm* — Larry Liberchuk

(57) ABSTRACT

The present invention relates to patient positioning. In order to facilitate patient positioning, an apparatus is provided that comprises an input unit, a processing unit, and an output unit. The input unit is configured to receive an X-ray image of an anatomy of interest of a patient obtained from a first image acquisition and a target set of pose parameters describing a target position of the anatomy of interest for image acquisition. The processing unit is configured to detect the anatomy of interest in the X-ray image, to determine a set of pose parameters describing a current position of the detected anatomy of interest in the first image acquisition, to determine a difference between the determined set of pose parameters and the target set of pose parameters, and to construct a trajectory that defines a sequence of sets of pose parameters for bringing the anatomy of interest from the current position to the target (Continued)

position, if the difference is equal to or greater than a pre-defined threshold. The processing unit is further configured to generate a series of X-ray images according to the received X-ray image and the sequence of sets of pose parameters in the trajectory to synthesize a virtual fluoroscopic image sequence of frames representing an animated radio graphic imaging during re-positioning of the patient. The output unit is configured to provide the synthetic Virtual fluoroscopic image sequence for positioning guidance for a second image acquisition.

13 Claims, 4 Drawing Sheets

(56) References Cited

OTHER PUBLICATIONS

Kausch L. et al., "C-Arm Positioning for Spinal Standard Projections in Different Intra-Operative Settings", Sep. 21, 2021 (Sep. 21, 2021), Computer Vision—ECCV 2020 : 16th European Conference, Glasgow, UK, Aug. 23-28, 2020 : Proceedings; [Lecture Notes in Computer Science; ISSN 0302-9743], Springer International Publishing, Cham, pp. 352-362, XP047610967.

Touchette M. et al., "The Effect of Artificial X-Rays on C-Arm Positioning Performance in a Simulated Orthopaedic Surgical Setting", International Journal of Computer Assisted Radiology and Surgery, vol. 16, No. 1, Nov. 4, 2020 (Nov. 4, 2020), pp. 11-22, XP037344295.

Krönke et al., "CNN-Based Pose-Estimation of Musculoskeletal X-Ray Images", OCUPAI, Jun. 1, 2021.

Haynes K. et al., "Fluoroscopic vs Blind Positioning: Comparing Entrance Skin Exposure", Radiologic Technology, vol. 81, No. 1, pp. 15-23, Sep.-Oct. 2009.

Krönke S. et al., "CNN-Based Pose Estimation for Assessing Quality of Ankle-Joint X-Ray Images", Medical Imaging 2022: Image Processing, vol. 12032. SPIE, 2022.

Nguyen G. et al., "Machine Learning and Deep Learning Frameworks and Libraries for Large-Scale Data Mining: A Survey", Artificial Intelligence Review, vol. 52, Issue 1, pp. 77-124, Jun. 2019.

* cited by examiner

FLUOROSCOPIC POSITIONING GUIDANCE

FIELD OF THE INVENTION

The present invention generally relates to patient positioning, and in particular to an apparatus and a method for positioning guidance for image acquisition, to an X-ray imaging system, to a computer program product, and to a computer-readable medium.

BACKGROUND OF THE INVENTION

Patient positioning is one of the most important quality aspect in radiology. It takes skills and experience to position a patient properly. Especially in musculoskeletal acquisitions it may take several attempts until the image is of sufficient quality.

SUMMARY OF THE INVENTION

There may, therefore, be a need to facilitate patient positioning.

The object of the present invention is solved by the subject-matter of the independent claims. Further embodiments and advantages of the invention are incorporated in the dependent claims. Furthermore, it shall be noted that all embodiments of the present invention concerning a method might be carried out with the order of the steps as described, nevertheless this has not to be the only and essential order of the steps of the method as presented herein. The method disclosed herein can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to a first aspect of the present invention, there is provided an apparatus for positioning guidance for image acquisition. The apparatus comprises an input unit, a processing unit, and an output unit. The input unit is configured to receive an X-ray image of an anatomy of interest of a patient obtained from a first image acquisition and a target set of pose parameters describing a target position of the anatomy of interest for image acquisition. The processing unit is configured to detect the anatomy of interest in the X-ray image, to determine a set of pose parameters describing a current position of the detected anatomy of interest in the first image acquisition, to determine a difference between the determined set of pose parameters and the target set of pose parameters, and to construct a trajectory that defines a sequence of sets of pose parameters for bringing the anatomy of interest from the current position to the target position, if the difference is equal to or greater than a pre-defined threshold. The processing unit is further configured to generate a series of X-ray images according to the received X-ray image and the sequence of sets of pose parameters in the trajectory to synthesize a virtual fluoroscopic image sequence of frames representing an animated radiographic imaging during re-positioning of the patient. The output unit is configured to provide the synthetic virtual fluoroscopic image sequence for positioning guidance for a second image acquisition.

The apparatus as described herein presents a synthetic X-ray sequence, also referred to as virtual fluoroscopic sequence, which renders the X-ray positioning from actual real positioning to a desired positioning of the patient indicating exactly the impact of the re-positioning.

Synthesizing a fluoroscopic sequence from a single X-ray and some model parameters is technically challenging. However, with the method available to estimate all pose parameters each given radiograph from an exam class (e.g. knee lateral) can be embedded in a multidimensional quality space spanned by these parameters. A generative model may be trained with single such images but advantageously with tuples of such images from an acquisition session of a patient with multiple positions. In an alternative example, this generative model may be trained using three-dimensional (3D) images of the anatomy, which may be the rendered in the target two-dimensional (2D) space. This generative model is used to regress deviations from a given real radiograph where the target parameters deviate from the real detected parameters.

A trajectory from observed to target parameter setting is constructed such that it follows a certain choreography or plot where changes of some parameters are done separately, and others are done simultaneously. For example, first in-plane displacement (central beam position) and collimation (field of view) are changed and then in-plane rotation is changed, then the other two remaining angles (rotation and angulation) are simultaneously changed, finally joint flexion is changed. In an alternative embodiment, the trajectory may be specified using an interactive operator interface, where re-positioning alternatives can be intuitively simulated and compared by the user, and their effects then observed in the resulting fluoroscopy sequence.

The fluoroscopic sequence is created by generating a series of X-ray images according to the input image and the plot which defines the set of parameters for each image in the series, starting from the actual parameter set and ending with the recommended parameter set. The resulting video may appear like a fluoroscopic image sequence of all required positioning changes to be taken to reproduce the recommended setting, however, at no cost of additional X-ray dose.

In some examples, the virtual fluoroscopic sequence may be used as a feedback to the technician after a first acquisition was rejected by quality control in the context of the Radiology Assistant. In this case, the animation is related to that existing image of the patient, and the target position of the anatomy of interest is a standard position recommended for this kind of acquisition.

In some examples, it could alternatively be also based on a standard position from which a deviating known position is required to be taken. In this case, the target position of the anatomy of interest is the deviating known position.

Although the following discussion is focused on the situation that the virtual fluoroscopic sequence is used as a feedback to the technician after a first acquisition was rejected by quality control in the context of the Radiology Assistant by way of example, it can be appreciated that the target position of the anatomy of interest may be any desired position and can be defined differently for other applications.

With the apparatus and method as described herein, no technologist has to leave the operation room to position the patient. Further, the virtual fluoroscopic sequence requires no additional X-ray dose during re-positioning.

According to an exemplary embodiment of the present invention, the processing unit is configured to augment the synthetic virtual fluoroscopic image sequence with an annotation indicative of a required movement of detected anatomy of interest.

In other words, the X-ray sequence may be complemented by additional graphical representations of the re-positioning changes, for example, a surface-based rendering of the anatomical elements and the re-positioning thereof.

According to an exemplary embodiment of the present invention, the annotation comprises at least one of an axis that follows a movement of the anatomy of interest along the trajectory and an angle or sub manifold spanned by the axis over the time of the sequence.

According to an exemplary embodiment of the present invention, the processing unit is configured to register a deformable model of the detected anatomy of interest to the received X-ray image, to adapt the deformable model of the detected anatomy of interest according to the sequence of sets of pose parameters in the trajectory, and to augment the synthetic virtual fluoroscopic image sequence with the adapted deformable model in each frame.

According to an exemplary embodiment of the present invention, the processing unit is configured to highlight a landmark and/or a key point on the detected anatomy of interest and render a movement of the highlighted landmark and/or key point in the synthetic virtual fluoroscopic image sequence.

According to an exemplary embodiment of the present invention, the processing unit is configured to apply a generative model to generate the series of X-ray images, wherein the generative model has been trained on training data.

Examples of the generative model may include, but are not limited to, a probabilistic framework and a deep encoder-decoder network architecture. An exemplary deep encoder-decoder network architecture will be explained in detail with respect to the example shown in FIG. 3.

According to an exemplary embodiment of the present invention, the training data comprises a plurality of three-dimensional (3D) images of the anatomy of interest.

According to an exemplary embodiment of the present invention, the training data comprises a plurality of two-dimensional (2D) images of the anatomy of interest and pose parameters derived from the two-dimensional images.

According to a second aspect of the present invention, there is provided an X-ray imaging system. The X-ray imaging system comprises an X-ray imaging device configured to acquire an X-ray image of an anatomy of interest of a patient. The X-ray imaging system additionally comprises an apparatus according to the first aspect, which is configured to provide, based on the acquired X-ray image of the anatomy of interest, a synthetic virtual fluoroscopic image sequence for positioning guidance for a next image acquisition. The X-ray imaging system further comprises a display configured to display the synthetic virtual fluoroscopic image sequence.

This will be explained hereinafter and in particular with respect to the example shown in FIG. 2.

According to a third aspect of the present invention, there is provided a method for positioning guidance for image acquisition. The method comprises the following steps:

receiving an X-ray image of an anatomy of interest of a patient obtained from a first image acquisition;

receiving a target set of pose parameters describing a target position of the anatomy of interest for image acquisition;

detecting the anatomy of interest in the X-ray image;

determining a set of pose parameters describing a current position of the detected anatomy of interest in the first image acquisition;

determining a difference between the determined set of pose parameters and the target set of pose parameters;

constructing a trajectory that defines a sequence of sets of pose parameters for bringing the anatomy of interest from the current position to the target position, if the difference is equal to or greater than a pre-defined threshold;

generating a series of X-ray images according to the received X-ray image and the sequence of sets of pose parameters in the trajectory to synthesize a virtual fluoroscopic image sequence of frames representing an animated radiographic imaging during re-positioning of the patient; and providing the synthetic virtual fluoroscopic image sequence for positioning guidance for a second image acquisition.

This will be explained hereinafter and in particular with respect to the example shown in FIG. 4.

According to an exemplary embodiment of the present invention, the method further comprises the step of augmenting the synthetic virtual fluoroscopic image sequence with an annotation indicative of a required movement of detected anatomy of interest.

According to an exemplary embodiment of the present invention, the method further comprises the steps of registering a deformable model of the detected anatomy of interest to the received X-ray image, adapting the deformable model of the detected anatomy of interest according to the sequence of sets of pose parameters in the trajectory, and augmenting the synthetic virtual fluoroscopic image sequence with the adapted deformable model in each frame.

According to an exemplary example of the present invention, the method further comprises the step of displaying the synthetic virtual fluoroscopic image sequence for positioning guidance for a second image acquisition.

According to another aspect of the present invention, there is provided a computer program product comprising instructions to cause the apparatus of the first aspect or the system of the second aspect to execute the steps of the method of the third aspect.

According to a further aspect of the present invention, there is provided a computer-readable medium having stored thereon the computer program.

As used herein, the term "patient" may include e.g., a human subject, and an animal subject.

As used herein, the term "pose parameters" may also be referred to as "positioning parameters". The pose parameters may describe the position, orientation, and scale of several anatomical landmarks of the anatomy of interest.

As used herein, the term "machine learning model", may refer to a statistical method that enables machines to "learn" tasks from data without explicitly programming, relying on patterns in the data instead. For example, the machine learning model may be a deep learning model. Deep learning is a subset of machine learning modeled loosely on the neural pathways of the human brain. Deep refers to the multiple layers between the input and output layers. In deep learning, the algorithm automatically learns what features are useful. A general introduction into machine learning and corresponding software frameworks is described in "Machine Learning and Deep Learning frameworks and libraries for large-scale data mining: a survey"; Artificial Intelligence Review; Giang Nguyen et al., June 2019, Volume 52, Issue 1, pp 77-124.

These and other features of the present invention will become apparent from and elucidated with reference to the embodiments described hereinafter.

BRIEF DESCRIPTION OF THE DRAWINGS

Exemplary embodiments of the invention will be described in the following with reference to the following drawings.

The figures are merely schematic representations and serve only to illustrate embodiments of the invention. Identical or equivalent elements are in principle provided with the same reference signs.

DETAILED DESCRIPTION OF EMBODIMENTS

Proper patient positioning is one of the pre-requisites of a diagnostic radiograph and is a typical challenge to achieve in daily clinical routine. Often several acquisitions are required until the pose is sufficient for the required image quality. Visual feedback on the previous image is highly appreciated to correct any errors made and to ensure an improved positioning at the next acquisition.

Various methods supported by artificial intelligence have been proposed to estimate relevant positioning parameters from a given radiograph. These estimated positioning parameters may be compared with the ideal parameters recommended for this kind of acquisition to assess the quality. Also recommendations may be derived how to change the parameters in order to improve the quality.

In order to visualize the indicated change of these parameters based on the current image, a well-known method places some icons into the image to indicate changes to be made by arrows or by showing both actual and desired position of an object. Such graphical representations may help indicating what needs to be changed, but annotating the given image with such graphical icons may not be the optimal way to visualize it. Pre-positioning using fluoroscopy is another known method for remote positioning. The advantage is that for combined RF/DxR systems, no technologist has to leave the operation room to position the patient, however, at the cost of additional X-ray dose during positioning.

Towards this end, an apparatus, an X-ray imaging system, and a method are provided utilizing an alternative approach showing the required changes in positioning by simulating an animated radiographic imaging during re-positioning of the patient. The virtual fluoroscopic sequence starts with the current image, shows all the changes that are required, and ends with the radiograph of the recommended positioning. This sequence may also be complemented by additional graphical representations of the re-positioning changes, for example a surface-based rendering of the anatomical elements and the re-positioning thereof. The virtual fluoroscopic sequence may be used as a feedback to the technician after a first acquisition was rejected by quality control in the context of the Radiology Assistant. In this case the animation is related to that existing image of the patient. It could alternatively be also based on a standard position from which a deviating known position is required to be taken.

Figure 1:
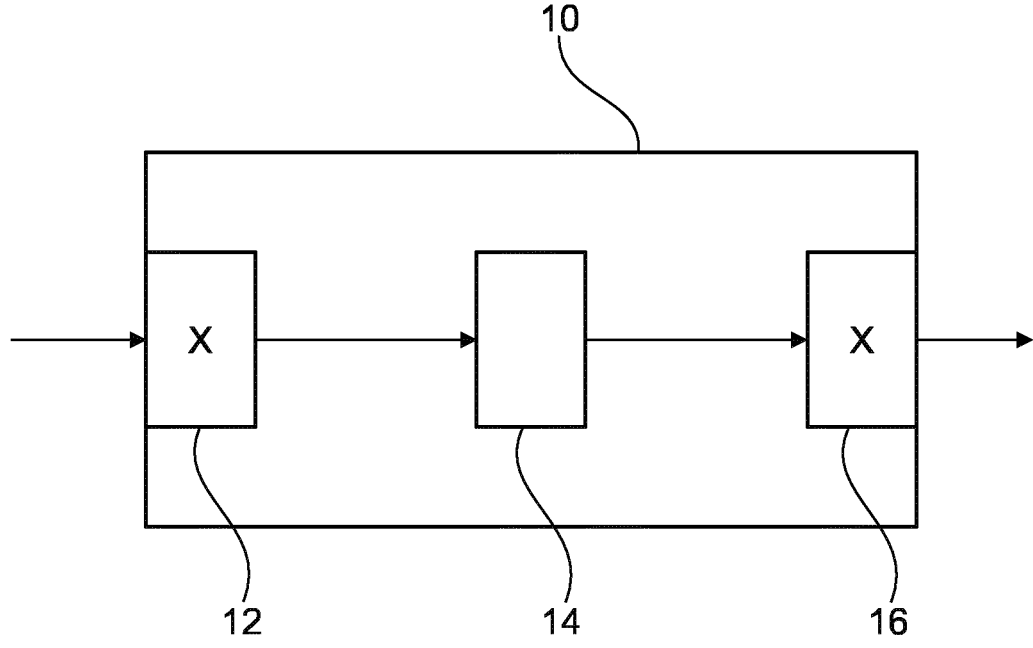
FIG. 1 illustrates an exemplary apparatus for positioning guidance for image acquisition.

FIG. 1 illustrates an exemplary apparatus 10 for positioning guidance for image acquisition. The exemplary apparatus 10 comprises an input unit 12, a processing unit 14, and an output unit 16.

In general, the apparatus 10 may comprise various physical and/or logical components for communicating and manipulating information, which may be implemented as hardware components (e.g., computing devices, processors, logic devices), executable computer program instructions (e.g., firmware, software) to be executed by various hardware components, or any combination thereof, as desired for a given set of design parameters or performance constraints. Although FIG. 1 may show a limited number of components by way of example, it can be appreciated that a greater or a fewer number of components may be employed for a given implementation.

In some implementations, the apparatus 10 may be embodied as, or in, a device or apparatus, such as a server, workstation, or mobile device. The apparatus 10 may comprise one or more microprocessors or computer processors, which execute appropriate software. The processing unit 14 of the apparatus 10 may be embodied by one or more of these processors. The software may have been downloaded and/or stored in a corresponding memory, e.g., a volatile memory such as RAM or anon-volatile memory such as flash. The software may comprise instructions configuring the one or more processors to perform the functions as described herein.

It is noted that the apparatus 10 may be implemented with or without employing a processor, and also may be implemented as a combination of dedicated hardware to perform some functions and a processor (e.g., one or more programmed microprocessors and associated circuitry) to perform other functions. For example, the functional units of the apparatus 10, e.g., the input unit 12, the one or more processing units 14, and the output unit 16 may be implemented in the device or apparatus in the form of programmable logic, e.g., as a Field-Programmable Gate Array (FPGA). In general, each functional unit of the apparatus may be implemented in the form of a circuit.

In some implementations, the apparatus 10 may also be implemented in a distributed manner. For example, some or all units of the apparatus 10 may be arranged as separate modules in a distributed architecture and connected in a suitable communication network, such as a 3rd Generation Partnership Project (3GPP) network, a Long Term Evolution (LTE) network, Internet, LAN (Local Area Network), Wireless LAN (Local Area Network), WAN (Wide Area Network), and the like.

The operation of the apparatus 10 will be explained in detail hereinafter and in particular with respect to the system shown in FIG. 2 and the method shown in FIG. 4.

Figure 2:
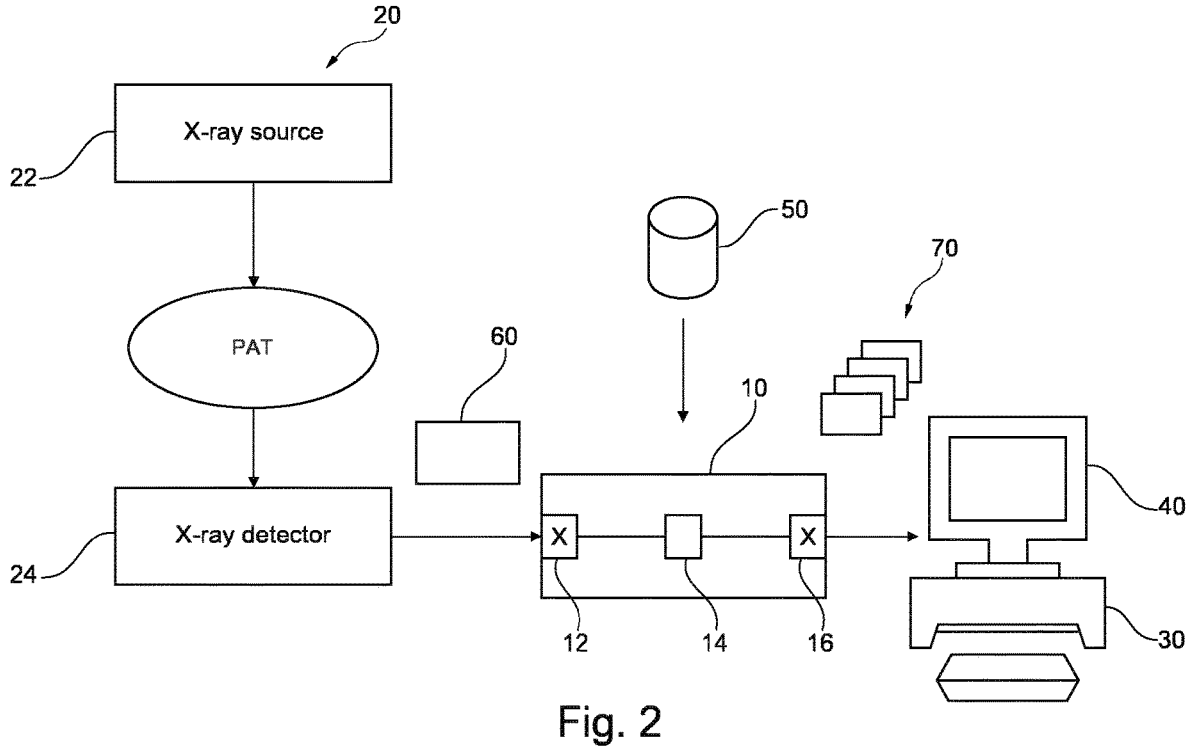
FIG. 2 illustrates an exemplary X-ray imaging system.

FIG. 2 shows schematically an exemplary X-ray imaging system 100. The exemplary X-ray imaging system 100 comprises the apparatus 10 as shown in FIG. 1, an X-ray imaging device 20, a system console 30, a display 40, and a database 50.

The X-ray imaging device 20 comprises an X-ray source 22 and an X-ray detector 24. The X-ray detector 24 is spaced from the X-ray source 22 to accommodate a patient PAT to be imaged. In some examples, the X-ray imaging device 20 may be of the C-arm type and the patient PAT may be lying on an examination table. In some examples, e.g. in a chest radiography examination, the patient PAT may stand facing a flat surface behind which is the X-ray detector 24.

In general, during an image acquisition, a collimated X-ray beam emits from the X-ray source 22, passes through the patient PAT at a region of interest (ROI), experiences attenuation by interaction with matter therein, and the attenuated beam then strikes the surface of the X-ray detector 24. The density of the organic material making up the ROI determines the level of attenuation. High-density material (such as bone) causes higher attenuation than less dense materials (such as tissue). The registered digital values for the X-ray are then consolidated into an array of digital values forming an X-ray projection image for a given acquisition time and projection direction.

Overall operation of the X-ray imaging device 20 may be controlled by an operator from the system console 30. The system console 30 may be coupled to a display 40 on which the acquired X-ray images or imager settings may be viewed or reviewed. An operator such as a medical lab technical can control via the system console 30 an image acquisition run by releasing individual X-ray exposures for example by actuating a joy stick or pedal or other suitable input means coupled to the system console 40.

In operation, the patient PAT is positioned e.g. with the help of a technologist for a first image acquisition. For example, the patient PAT is positioned for knee radiographs to assess the bony structure of the knee and e.g. to define the presence of fractures and also to assess for degenerative disease within the joint.

Figure 3:
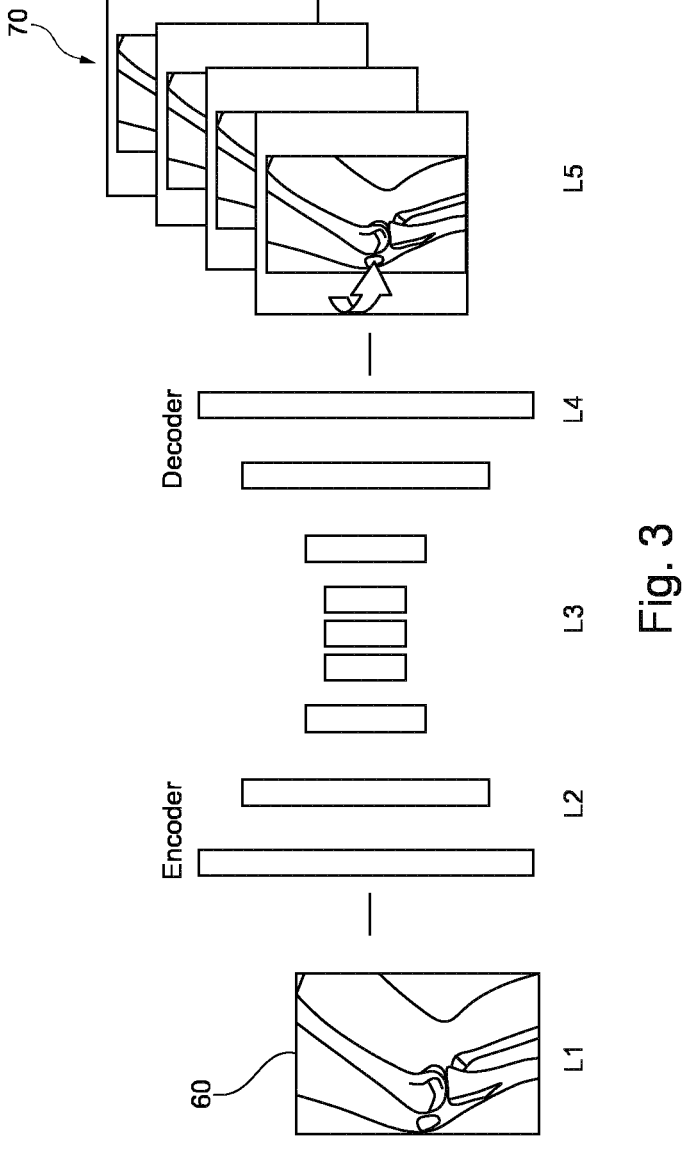
FIG. 3 illustrates an exemplary generative model.

Patient positioning is important in the setting of musculoskeletal imaging, such as the exemplary knee radiographs shown in FIG. 3. Multiple projections assist in characterizing fractures, joint alignment, and other pathologies such as arthritis and tumors. Non-standard projections can potentially lead to missed diagnoses and associated morbidity. The importance of standard flexion and extension positioning is paramount, considering these positions can affect the appearance of standard anatomy on radiographs. The potential for ascribing a diagnosis in the setting of a normal study (i.e., a "false positive") is important to consider when anatomy appears altered due to non-standard positioning and projections.

Towards this end, the apparatus 10 is provided for positioning guidance for image acquisition. As described above, the apparatus 10 may be any computing device, including desktop and laptop computers, smartphones, tablets, etc. The apparatus 10 may be a general-purpose device or a device with a dedicated unit of equipment suitable for providing the functionality as described herein. In the example of FIG. 2, the components of the apparatus 10 are shown as integrated in one single unit. However, in alternative examples, some or all components may be arranged as separate modules in a distributed architecture and connected in a suitable communication network. The apparatus 10 and its components may be arranged as dedicated FPGAs or as hardwired standalone chips, such as the apparatus shown in FIG. 2. In some examples (not shown), the apparatus 10 or some of its components may be resident in the system console 30 running as software routines.

The input unit 12 of the apparatus 10 is configured to receive an X-ray image 60 of an anatomy of interest of a patient obtained from the first image acquisition. Examples of the anatomy of interest may include, but are not limited to, chest, hand, wrist, forearm, elbow, humerus, shoulder, foot, ankle, tibia-fibula, or any other anatomy of interest of a patient.

The input unit 12 of the apparatus 10 is further configured to receive a target set of pose parameters describing a target position of the anatomy of interest for image acquisition. For example, the target set of pose parameters are ideal parameters recommended for this kind of image acquisition. In some examples, as shown in FIG. 2, the target set of pose parameters may be retrieved from the database 50 that stores a plurality of target sets of pose parameters for different anatomies of interest including, but not limited, to chest, hand, wrist, forearm, elbow, humerus, shoulder, foot, ankle, tibia-fibula, or any other anatomy of interest of a patient.

The target set of pose parameters may be defined utilizing positioning protocols that are based on empirically derived standards for a particular acquisition. For example, the target set of pose parameters for knee radiographs may include a target rotation parameter, a target angulation parameter, a target flexion parameter, a target field of view, and a target central beam parameter. For instance, for a standard lateral knee protocol, these parameters are those that position a standard knee model fit to the bones in the image such that its condyles overlap perfectly with each other when projected onto the detector. An ideal flexion angle is chosen, typically between full flexion and full extension.

The processing unit 14 is configured to detect the anatomy of interest in the X-ray image. For example, a segmentation module may be applied to segment the anatomy of interest in the X-ray image. Examples of the segmentation module may include, but are not limited to, fully convolutional neural networks (FCNS), U-Net, or generative adversarial network (GAN), which will be briefly discussed below.

FCN is derived from a CNN-based segmentation network. It trains end-to-end, pixels-to-pixels digital input images for a given segmentation task. The idea of FCN is to build convolutional layers without any fully connected layers and to produce an output size that corresponds to the input. The input data feature map is encoded and decoded using transposed convolution to attain the same size output. As the network decodes, the skip connection sums pre-extracted feature maps to recover the spatial information during pooling operations.

U-Net is an FCN that relies on the use of data augmentation aided toward precise localization in biomedical image segmentation. The U-Net architecture includes multiple up-sampling layers, skip connection that concatenates feature maps, and learnable weight filters. The result shows outstanding performance in both biomedical image segmentation and crack detection.

GAN-based segmentation models can be considered as a two-player game between a generator, which learns how to generate samples resembling real data, and a discriminator, which learns how to discriminate between real and generated data. Both the generator and the discriminator cost functions are minimized simultaneously. The iterative minimization of cost functions eventually leads to a Nash equilibrium where neither can further unilaterally minimize its cost function. In the end, the GAN discriminator provides an abstract unsupervised representation of the input images.

The processing unit 14 is further configured to determine a set of pose parameters describing a current position of the detected anatomy of interest in the first image acquisition. A method supported by artificial intelligence may be used to estimate relevant positioning parameters from a given radiograph. For example, convolutional neuronal networks (CNNs) may be applied to determine the set of pose parameters with a two-step algorithm. In a first step, pose-discriminative features (e.g. outer silhouettes, inner contours) are detected by a CNN. Thereafter, another CNN maps these features in form of binary segmentation masks to all pose parameters of interest. For a detailed discussion concerning the two-step algorithm, reference is made to the following publication: Krönke et al. CNN-based pose-estimation of musculoskeletal X-ray images. OCUPAI 2021. With the method available to estimate all pose parameters, each given radiograph from an exam class (e.g. knee lateral) can be embedded in a multidimensional quality space spanned by these parameters.

The processing unit 14 is further configured to determine a difference between the determined set of pose parameters and the target set of pose parameters. In other words, the determined set of pose parameters can be compared with the ideal parameters recommended for this kind of acquisition to assess the quality.

The processing unit 14 is further configured to construct a trajectory that defines a sequence of sets of pose parameters for bringing the anatomy of interest from the current position to the target position, if the difference is equal to or greater than a pre-defined threshold.

In some examples, the pre-defined threshold may be a maximum allowable range centered around the target set of pose parameters, within which the pose is sufficient for a required image quality. Also taken the knee radiographs as an example, the maximum allowable range may comprise a maximum allowable range of in-plane displacement centered around the target central beam position parameter, a maximum allowable range of collimation centered around the target field of view, a maximum allowable range of angles centered around the target rotation parameter, a maximum allowable range of angles centered around the target angulation, and a maximum allowable range of flexion around the target joint flexion. The maximum allowable range may be defined in a multidimensional quality space spanned by these parameters. In some examples, the pre-defined threshold may be a threshold less than the maximum allowable range centered around the target set of pose parameters. The pre-defined threshold may be set and adjusted by a user via a user interface.

The trajectory from observed to the target parameter setting may be constructed such that it follows a certain choreography or plot where changes of some pose parameters may be done separately, and others may be done simultaneously. In the example of knee radiographs, first in-plane displacement, i.e. central beam position, and collimation, i.e. field of view, may be changed and then in-plane rotation may be changed. Afterwards, the other two remaining angles, i.e. rotation and angulation, may be simultaneously changed. In some examples, the trajectory may be derived from previously monitored movement trajectory of the patient or other patients during re-positioning. It may be beneficial that the derived trajectory reflects the natural movement trajectory of the patient, and thus prevent the patient from being hurt due to unnatural movement trajectory. This may be done by using a camera to acquire a sequence of images to capture the movement trajectory of the patient and/or other patients during patient re-positioning in previous examinations. The acquired sequence of images may be used to train a machine learning model to estimate changes of pose parameters from a given difference between the observed parameter setting and the target parameter setting. In some examples, the trajectory may be specified using an interactive operator interface, such as the system console 40, where re-positioning alternatives can be intuitively simulated and compared by the user, and their effects the observed in the resulting fluoroscopy sequence.

The processing unit 14 is further configured to generate a series of X-ray images according to the received X-ray image and the sequence of sets of pose parameters in the trajectory to synthesize a virtual fluoroscopic image sequence of frames representing an animated radiographic imaging during re-positioning of the patient. In other words, the fluoroscopic sequence is created by generating a series of X-ray images according to the input image and the plot which defines the set of parameters for each image in the series, starting from the actual parameter set and ending with the recommended parameter set. The resulting video may appear like a fluoroscopic image sequence of all required positioning changes to be taken to reproduce the recommended setting.

For example, a generative model may be trained to reproduce a mapping between the X-ray image having the observed posed parameter setting and X-ray images having the sequence of sets of pose parameters for bringing the anatomy of interest from the current position to the target position. In other words, from the acquired X-ray image, the generative model may be used to generate additional synthetic X-ray images from a hypothetical acquisition session of the patient with multiple positions.

The generative model may be trained with single such images but advantageously with tuples of such images from an acquisition session of a patient with multiple positions. In an alternative example, the generative model may be trained using 3D images of the anatomy, which may be the rendered in the target 2D (image) space. This generative model may be used to regress deviations from a given real radiograph where the target parameters deviate from the real detected parameters.

In some examples, the generative model may include a generative model of image synthesis using a probabilistic framework. In some examples, the generative model may include a deep encoder-decoder network architecture.

FIG. 3 shows an example of a generative model that has an encoder decoder network architecture. The architecture relies on finding a mapping between an input image and a desired image. The input image is an acquired X-ray image 60. The desired image is a sequence of synthetic X-ray images 70 from a hypothetical acquisition session of the patient with multiple positions.

In particular, the input layer L1 receives an X-ray image acquired from a real acquisition session of the patient with a first position. Then, layers L2 and L3 aim to encode the input. The subsequent layers L4 and L5 essentially decode the information coming from the previous layers, providing at the output a synthetic X-ray image acquired from a hypothetical acquisition session of the patient with a second position different from the first position. The weights per-layer may be pre-trained based on a training dataset comprising a plurality of pairs of acquired X-ray images having different sets of pose parameters. The pre-training may rely on unsupervised learning.

In the inference phase, an X-ray image acquired from a real acquisition session of the patient with a first position is provided to the layer L1 and into the entire network. The activations on the layer L5 are the output of the network and represent the actual synthetic X-ray image acquired from a hypothetical acquisition session of the patient with a second position different from the first position. Although FIG. 3 may show a limited number of X-ray images in the sequence by way of example, it can be appreciated that a greater or a fewer number of X-ray images may be generated for a given implementation.

Turning back to FIG. 2, the output unit 16 is configured to provide the synthetic virtual fluoroscopic image sequence 70 for positioning guidance for a second image acquisition, e.g. to the display 40 on the system console 30.

As the images are synthetically rendered, they may be augmented by annotations. In the following, some exemplary annotations will be discussed. These exemplary annotations may be combined with each other.

In an example, the synthetic X-ray images may be augmented by annotations like axes that follow the movement of their bones. Also angles or sub manifolds spanned by such an axis over the time of the sequence may be shown to illustrate the overall changes to be made. For example, as shown in FIG. 3, an icon is placed into the image to indicate changes to be made by arrows.

In another example, a deformable and parametrized 3D model may be registered to the given X-ray image in each frame. Subsequently, the trajectory described above can feed an animation of this model resulting in a fully synthetic sequence of frames. In each frame, a rendering of the adapted 3D model may be presented from the perspective of the tube head or a prediction for the most salient contours when projecting the model under the pose corresponding to the respective frame.

As a further example, special landmarks and keypoints of the bone surface may be highlighted to provide additional guidance and orientation for the radiographer (e.g. those being palpable from the outside). The movement of theses keypoints may be rendered in the fluoroscopic image sequence.

Figure 4:
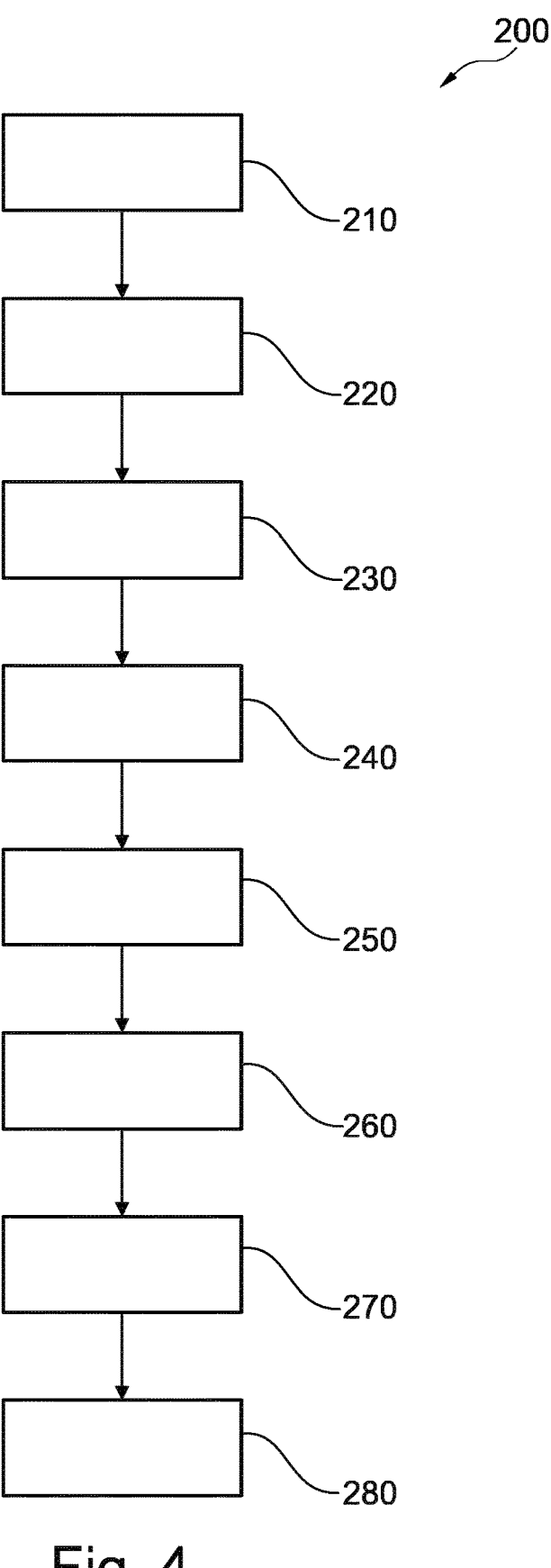
FIG. 4 shows a flow chart describing an exemplary method for positioning guidance for image acquisition.

FIG. 4 illustrates a flow chart describing an exemplary method 200 for positioning guidance for image acquisition. The method 200 may be implemented as a device, module or related component in a set of logic instructions stored in a non-transitory machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof. For example, computer program code to carry out operations shown in the method 100 may be written in any combination of one or more programming languages, including an object oriented programming language such as JAVA, SMALLTALK, C++, Python, or the like and conventional procedural programming languages, such as the "C" programming language or similar programming languages. For example, the method may be implemented as the apparatus 10 shown in FIG. 1 and FIG. 2.

At block 210, an X-ray image of an anatomy of interest of a patient obtained from a first image acquisition is received, e.g. by the exemplary apparatus 10 shown in FIG. 1 or FIG. 2. The X-ray image of the anatomy of interest of the patient may be acquired by the exemplary X-ray imaging device 20 shown in FIG. 2. Examples of the anatomy of interest may include, but are not limited to, chest, hand, wrist, forearm, elbow, humerus, shoulder, foot, ankle, and tibia-fibula.

At block 220, a target set of pose parameters is received. The target set of pose parameters describes a target position of the anatomy of interest for image acquisition. Take knee radiographs as an example, the target set of pose parameters may comprise a target rotation parameter, a target angulation parameter, a target flexion parameter, a target field of view, and a target central beam parameter. The target set of pose parameters may be retrieved from a database, e.g. database 50 shown in FIG. 2, which stores, for each anatomy of interest, a respective target set of pose parameters.

At block 230, the anatomy of interest in the X-ray image is detected. For example, a segmentation module, e.g. FCNS, U-Net, or GAN, may be applied to segment the anatomy of interest in the X-ray image.

At block 240, a set of pose parameters is determined describing a current position of the detected anatomy of interest in the first image acquisition. For example, a machine-learning model, such as CNN, may be used to estimate relevant positioning parameters from the given radiograph.

At block 250, a difference between the determined set of pose parameters and the target set of pose parameters. In other words, a deviation between the current positon and the target position is determined.

At block 260, a trajectory is constructed that defines a sequence of sets of pose parameters for bringing the anatomy of interest from the current position to the target position, if the difference is equal to or greater than a pre-defined threshold. The trajectory from observed to target parameter setting may be constructed such that it follows a certain choreography or plot where changes of some parameters are done separately, and others are done simultaneously. In an example, the trajectory may be determined using a trained machine learning model. In an alternative example, the trajectory may be specified using an interactive operator interface, where re-positioning alternatives can be intuitively simulated and compared by the user, and their effects then observed in the resulting fluoroscopy sequence.

At block 270, a series of X-ray images is generated according to the received X-ray image and the sequence of sets of pose parameters in the trajectory to synthesize a virtual fluoroscopic image sequence of frames representing an animated radiographic imaging during re-positioning of the patient. A generative model may be trained with single such images but advantageously with tuples of such images from an acquisition session of a patient with multiple positions. In an alternative example, this model is trained using 3D images of the anatomy, which may be the rendered in the target 2D space. This generative model is used to regress deviations from a given real radiograph where the target parameters deviate from the real detected parameters.

At block 280, the synthetic virtual fluoroscopic image sequence is provided for positioning guidance for a second image acquisition. For example, the synthetic virtual fluoroscopic image sequence may be displayed to the operator. The fluoroscopic image sequence may also be complemented by additional graphical representations of the re-positioning changes. For example, the fluoroscopic image sequence may be complemented by a surface-based rendering of the anatomical elements and the re-positioning thereof. This may be done by registering a deformable model of the detected anatomy of interest to the received X-ray image, adapting the deformable model of the detected anatomy of interest according to the sequence of sets of pose parameters in the trajectory, and augmenting the synthetic virtual fluoroscopic image sequence with the adapted deformable model in each frame.

The synthetic virtual fluoroscopic image sequence may be displayed for positioning guidance for a second image acquisition.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus.

The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for positioning guidance for image acquisition, comprising:
a memory that stores a plurality of instructions; and
a processor coupled to the memory and configured to execute the plurality of instructions to:
receive an X-ray image of an anatomy of interest of a patient obtained from a first image acquisition and a target set of pose parameters describing a target position of the anatomy of interest for image acquisition;
detect the anatomy of interest in the X-ray image;
determine a set of pose parameters describing a current position of the detected anatomy of interest in the first image acquisition;
determine a difference between the determined set of pose parameters and the target set of pose parameters;
construct a trajectory that defines a sequence of sets of pose parameters for bringing the anatomy of interest from the current position to the target position, if the difference is equal to or greater than a pre-defined threshold;
generate a series of X-ray images according to the received X-ray image and the sequence of sets of pose parameters in the trajectory to synthesize a virtual fluoroscopic image sequence of frames representing an animated radiographic imaging during re-positioning of the patient; and
provide the synthetic virtual fluoroscopic image sequence for positioning guidance for a second image acquisition.

2. The apparatus according to claim 1, wherein the processor is configured to augment the synthetic virtual fluoroscopic image sequence with an annotation indicative of a required movement of detected anatomy of interest.

3. The apparatus according to claim 2, wherein the annotation comprises:
an axis that follows a movement of the anatomy of interest along the trajectory; and/or
an angle or sub manifold spanned by the axis over the time of the sequence.

4. The apparatus according to claim 1, wherein the processor is configured to register a deformable model of the detected anatomy of interest to the received X-ray image, to adapt the deformable model of the detected anatomy of interest according to the sequence of sets of pose parameters in the trajectory, and to augment the synthetic virtual fluoroscopic image sequence with the adapted deformable model in each frame.

5. The apparatus according to claim 1, wherein the processor is configured to highlight a landmark and/or a key point on the detected anatomy of interest, and render a movement of the highlighted landmark and/or key point in the synthetic virtual fluoroscopic image sequence.

6. The apparatus according to claim 1, wherein the processor is configured to apply a generative model to generate the series of X-ray images, wherein the generative model has been trained on training data.

7. The apparatus according to claim 6, wherein the training data comprises a plurality of three-dimensional, 3D, images of the anatomy of interest.

8. The apparatus according to claim 6, wherein the training data comprises a plurality of two-dimensional images of the anatomy of interest and pose parameters derived from the two-dimensional images.

9. A method for positioning guidance for image acquisition, comprising:

receiving an X-ray image of an anatomy of interest of a patient obtained from a first image acquisition;

receiving a target set of pose parameters describing a target position of the anatomy of interest for image acquisition;

detecting the anatomy of interest in the X-ray image;

determining a set of pose parameters describing a current position of the detected anatomy of interest in the first image acquisition;

determining a difference between the determined set of pose parameters and the target set of pose parameters;

constructing a trajectory that defines a sequence of sets of pose parameters for bringing the anatomy of interest from the current position to the target position, if the difference is equal to or greater than a pre-defined threshold;

generating a series of X-ray images according to the received X-ray image and the sequence of sets of pose parameters in the trajectory to synthesize a virtual fluoroscopic image sequence of frames representing an animated radiographic imaging during re-positioning of the patient; and providing the synthetic virtual fluoroscopic image sequence for positioning guidance for a second image acquisition.

10. The method according to claim 9, further comprising:

augmenting the synthetic virtual fluoroscopic image sequence with an annotation indicative of a required movement of detected anatomy of interest.

11. The method according to claim 10, further comprising:

registering a deformable model of the detected anatomy of interest to the received X-ray image;

adapting the deformable model of the detected anatomy of interest according to the sequence of sets of pose parameters in the trajectory; and augmenting the synthetic virtual fluoroscopic image sequence with the adapted deformable model in each frame.

12. The method according to claim 9, further comprising:

displaying the synthetic virtual fluoroscopic image sequence for positioning guidance for a second image acquisition.

13. A non-transitory computer-readable medium comprising executable instructions which, when executed by at least one processor, cause the at least one processor to perform a method for positioning guidance for image acquisition, the method comprising:

receiving an X-ray image of an anatomy of interest of a patient obtained from a first image acquisition;

receiving a target set of pose parameters describing a target position of the anatomy of interest for image acquisition;

detecting the anatomy of interest in the X-ray image;

determining a set of pose parameters describing a current position of the detected anatomy of interest in the first image acquisition;

determining a difference between the determined set of pose parameters and the target set of pose parameters;

constructing a trajectory that defines a sequence of sets of pose parameters for bringing the anatomy of interest from the current position to the target position, if the difference is equal to or greater than a pre-defined threshold;

generating a series of X-ray images according to the received X-ray image and the sequence of sets of pose parameters in the trajectory to synthesize a virtual fluoroscopic image sequence of frames representing an animated radiographic imaging during re-positioning of the patient; and providing the synthetic virtual fluoroscopic image sequence for positioning guidance for a second image acquisition.

* * * * *